United States Patent
Argauer

(10) Patent No.: US 6,875,223 B2
(45) Date of Patent: Apr. 5, 2005

(54) LANCET FOR BLOOD EXTRACTION

(75) Inventor: Herbert Argauer, Pirk (DE)

(73) Assignee: Wilden AG, Regensburg (DE)

( * ) Notice: Subject to any disclaimer, the term of this patent is extended or adjusted under 35 U.S.C. 154(b) by 230 days.

(21) Appl. No.: 10/234,186

(22) Filed: Sep. 5, 2002

(65) Prior Publication Data

US 2003/0199891 A1 Oct. 23, 2003

(30) Foreign Application Priority Data

Sep. 5, 2001  (DE) ................................. 201 14 658 U

(51) Int. Cl.⁷ ............................................. A61B 17/34
(52) U.S. Cl. ..................................................... 606/181
(58) Field of Search ............................... 606/181, 182, 606/183, 167; 600/583; 604/192

(56) References Cited

U.S. PATENT DOCUMENTS

| 3,358,689 A | 12/1967 | Higgins |
| 2002/0151920 A1 * | 10/2002 | Marshall et al. ............ 606/181 |

FOREIGN PATENT DOCUMENTS

| DE | 197 18 081 A1 | 11/1998 |
| EP | 0 589 186 A1 | 3/1994 |
| GB | 2 352 403 A | 1/2001 |
| WO | WO 9602189 A1 | 2/1996 |
| WO | 99/27855 A1 | 6/1999 |

* cited by examiner

Primary Examiner—David O. Reip
Assistant Examiner—D. Jacob Davis
(74) Attorney, Agent, or Firm—Birch, Stewart, Kolasch & Birch, LLP

(57) ABSTRACT

A lancet for the extraction of blood includes a base portion of plastics material, a lancet needle of a metallic material held in the base portion and having a pointed end section protruding from the base portion, a head portion of plastics material integrally connected to the base portion by a preset breaking zone, and cooperating cam means on the base and head portions. The head portion can be removed from the base portion thereby exposing the pointed end section of the lancet needle by exerting a rotational force to one of the base and head portions relative to the other. The lancet needle is embedded in the head portion prior to the removal thereof. The cam means comprises pairs of cooperating cam sections on the base and head portions engaging with each other upon relative rotation between these portions for creating an axial movement of the head portion relative to the base portion thereby causing a rupture of the preset breaking zone.

8 Claims, 3 Drawing Sheets

LANCET FOR BLOOD EXTRACTION

FIELD OF THE INVENTION

The invention relates to a lancet for the extraction of blood and especially to one comprising a lancet needle of a metallic material that is held in a base portion of plastics material and has a pointed end section protruding out from the base portion, in which the pointed end section of the needle is further embedded in a head portion of plastics material connected to the base portion by a preset breaking zone such that the head portion can be removed from the base portion prior to use thereby exposing the pointed end section of the needle if a rotational force is exerted on one of said base and head portions relative to the other portion.

BACKGROUND OF THE INVENTION

Lancets of this type are known from e.g. EP-A-589186 and similar designs have been in practical use for a long time. The head portion, in which the pointed end section of the lancet needle protruding from the base portion is embedded, ensures that the pointed end section of the needle is kept in a sterile environment until the lancet is used. The previous practice when handling such lancets was to detach the head portion from the base portion prior to using the lancet by rotating the head portion by a certain amount relative to the base portion so that a breaking zone between these parts will rupture. Thereafter, a manual pulling force is exerted on the head portion while keeping more or less axial alignment of the lancet needle to the base portion in order to overcome a frictional force between the pointed end section of the needle and the head portion so that the head portion can be pulled-off the end section of the needle. However, it has been found in practice that the pointed end section of the lancet needle is frequently so tightly seated in the head portion that the entire lancet needle is sometimes withdrawn from the base portion in the course of the above described operation, or that the pulling forces that have to be applied are so large that if they are not effective exactly in the axial or longitudinal direction of the lancet needle the protruding end section of the needle might bend. Lancets of the present type are often used in conjunction with actuating means which enable a rapid mechanical movement of the pointed end section of the needle into a person's skin for the purposes of blood extraction. It has been found that when detaching the head portion, the base portion of the lancet held by clamping forces in the actuating means is frequently withdrawn therefrom rendering the lancet unusable.

SUMMARY OF THE INVENTION

An object of the invention is to produce a lancet of a type referred to above in which the head portion may be separated from the base portion without a risk of unwanted or damaging effects being exerted on the lancet needle when preparing the lancet for a blood extraction operation. Another object of the invention is to produce a lancet of a type referred to above which may be used in conjunction with actuating means without a risk of causing problems when handling the lancet by such actuating means.

In accordance with the invention, this object is achieved by a lancet for the extraction of blood, including a base portion of plastics material, a lancet needle of a metallic material held in said base portion and having a pointed end section protruding from the base portion, a head portion of plastics material being integrally connected to the base portion by a preset breaking zone and adapted to be removed from the base portion thereby exposing the pointed end section of the lancet needle by exerting a rotational force to one of said base and head portions relative to the other, the lancet needle being embedded in the head portion prior to the removal thereof, and cam means on said base and head portions engaging with each other upon relative rotation between the head and the base portions for creating an axial movement of the head portion relative to the base portion. Thus in a lancet according to the present invention cam means are provided between the head portion and the base portion for producing an axial movement of the head portion relative to the base portion during a relative rotation between the head and base portions. Rather than for exposing the end section by pulling the head portion off the end section of the needle in a more or less uncontrolled manner by hands as this was hitherto usually done, this pulling now can occur in a controlled manner in that the cam means of a lancet according to the present invention ensures a precise axial movement of the head portion away from the base portion whilst substantially relieving the lancet needle of axial forces prior to and during the process of detaching the head portion from the base portion, since the head portion continues to be supported on the base portion during this operation. Consequently, there is no risk of withdrawing the lancet needle from the base portion, or, of inadvertently withdrawing the base portion from an actuating means. Moreover, the cam means simultaneously has the function of an anti-buckling means in that it reliably prevents the pointed end section of the needle from being bent by external lateral forces exerted on the head portion. While means for preventing lateral deflection of the head portion by more than a certain amount are known, by the prior anti-buckling measures the above-mentioned problems in regard to the handling of the lancet by actuating means could not be overcome. In a lancet according to the present invention a complete detachment of the head portion from the base portion requires but a short rotary movement of the head portion relative to the base portion without a need for further action by a user. The cam means can easily be formed together with other parts of the lancet by a plastics injection moulding process resulting in a preferred one-piece construction of the lancet.

BRIEF DESCRIPTION OF THE DRAWINGS

The invention will be explained in more detail hereinafter with the aid of the drawing and a preferred embodiment thereof. In the drawing

DETAILED DESCRIPTION OF THE PREFERRED EMBODIMENT

Figure 1:
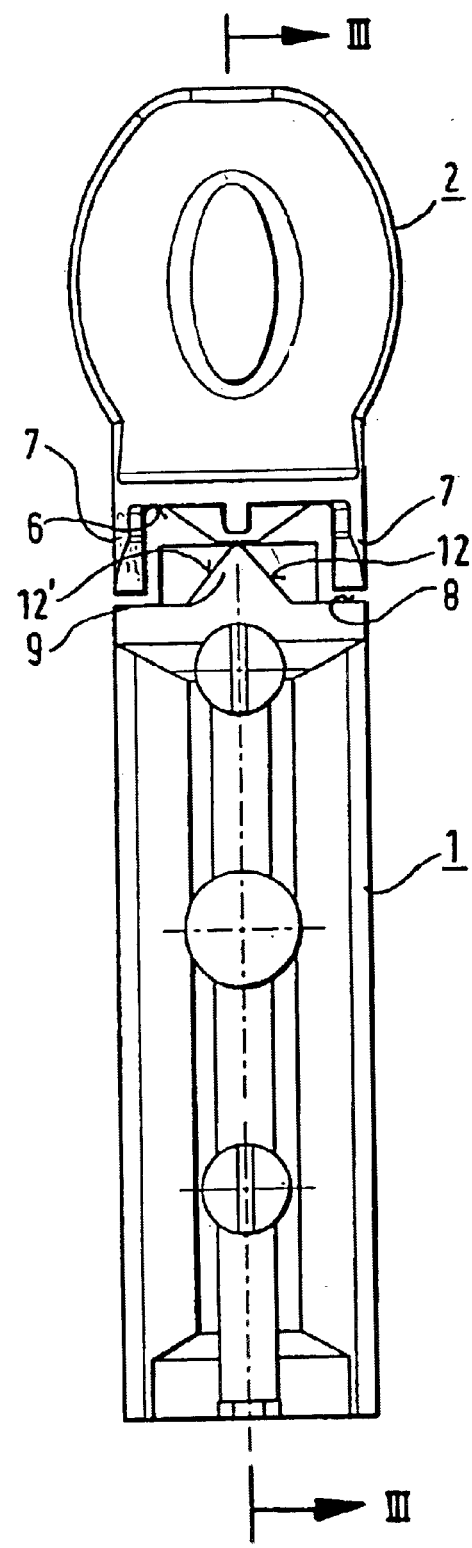
FIG. 1 is a side view of a lancet according to the invention
Figure 2:
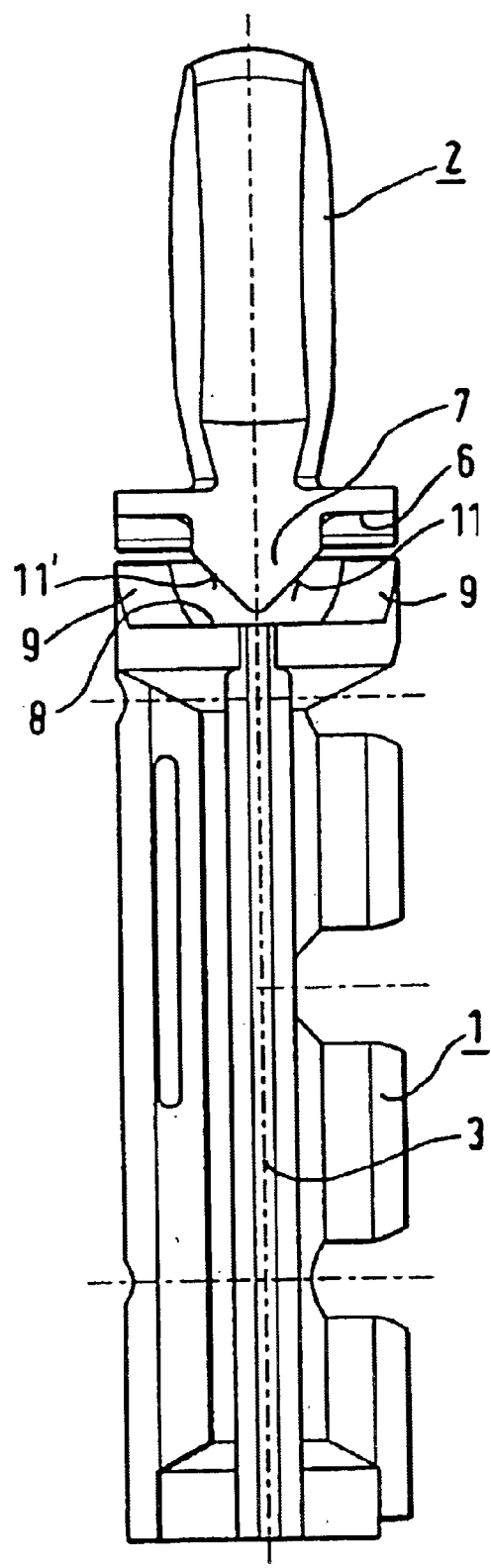
FIG. 2 is a view similar to FIG. 1 of the lancet after rotation through 90°.
Figure 3:
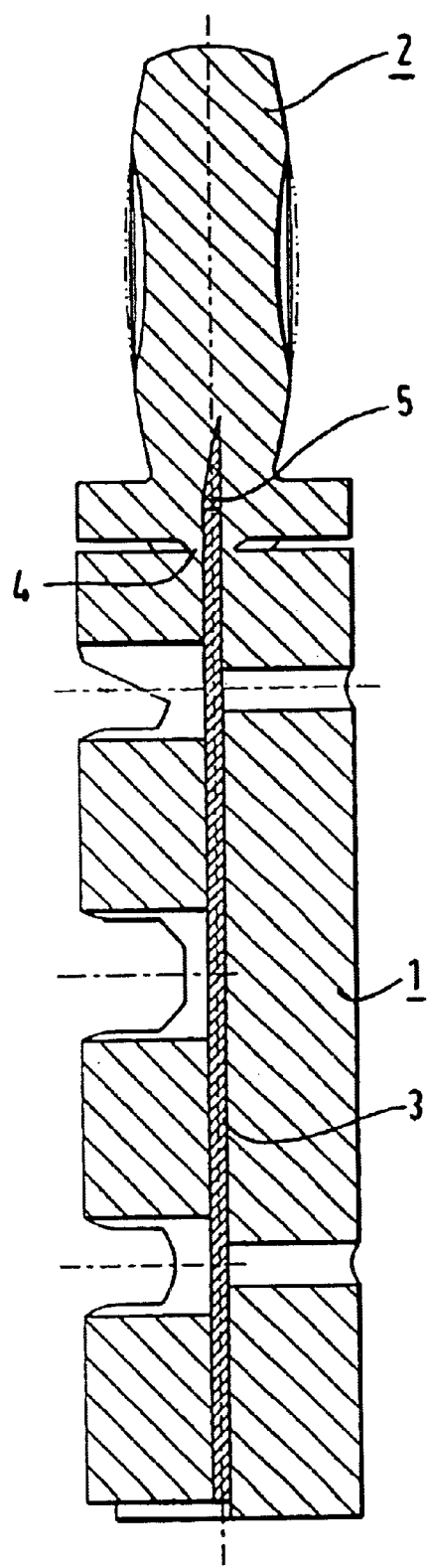
FIG. 3 is a longitudinal sectional view of the lancet along the section line III—III in FIG. 1.

The lancet according to the present invention is shown in FIG. 1 and comprises a base portion 1 and a head portion 2. A lancet needle 3 is firmly held in the base portion 1. The base portion 1 and the head portion 2 are integrally connected with each other at a preset severing or breaking zone 4 which is shown in FIG. 3. The base portion 1 and head portion 2 of the lancet preferably is an injection moulded integral part of a suitable plastics material such as a polyolefine, e.g. polypropylene or polyethylene, but other plastics materials could be used if so desired. The preset breaking zone 4 is designed such that it can be caused to sever under the effect of an external force in order to separate the head portion 2 from the base portion 1. The preset breaking zone 4 may be in the form of a peripherally extending narrowing of the cross-section or it may be formed by a plurality of peripherally distributed, axially extending breakable webs. Other suitable constructions of the preset breaking zone 4 could also be provided.

A pointed end section 5 of the lancet needle 3 protrudes out from the base portion 1 and is embed in the head portion 2 as long as the head portion 2 is connected to the base portion 1, i.e., when the preset breaking zone 4 is intact. Thereby the pointed end section 5 is hermetically sealed from external effects of the surroundings. The lancet needle 3 preferably is formed of a suitable metallic material such as a steel material. Whilst the lancet needle 3 is firmly seated in the base portion 1, the pointed end section 5 of the lancet needle 3 can be less firmly seated in the head portion 2 so that the head portion 2 can be separated from the pointed end section 5 of the lancet needle 3 after its removal from the base portion 1 without the need for a substantial force to be exerted on the lancet needle 3 during this operation. However, it is also within the scope of the invention for the pointed end section 5 of the lancet needle 3 to be more firmly seated in the head portion 2.

A pair of cam sections 7 protrude from an end face 6 of the head portion 2 in an axial direction towards an opposite end face 8 of the base portion 1, and another pair of cam sections 9 protrudes from the end face 8 of the base portion 1 in an axial direction towards the end face 7 of the head portion 2. The cam sections 7 and 9 of each pair are disposed diametrically relative to one another, in which the cam sections 7 of one pair can engage in the gaps between the cam sections 9 of the other pair when there is no external force effective on the lancet.

Each cam section 7, 9 preferably has a pointed gable-like configuration having, on each side of a vertex or top end, cam faces 11, 11' and 12, 12' which are inclined relative to the associated end face 6, 8 of the head portion 2 or the base portion 1, respectively. The inclined cam faces 11, 12 of adjacent cam sections 7, 9 engage with one another when there is a relative rotation between the head portion 2 and the base portion 1 for producing a controlled axial movement of the head portion 2 away from the base portion 1 and in addition thereto a movement in the peripheral direction or the direction of rotation when the adjacent cooperating cam faces 11, 12 slide upon one another. Accordingly, in the course of this operation, the head portion 2 will be moved axially away from the base portion 1 without an external axial pulling force having to be exerted on the head portion 2. The conversion of the rotational force into an axial movement of the head portion 2 may result in that the pointed end section 5 of the lancet needle 3 is completely exposed or in that it is at least freed to a sufficient extent that a small additional force suffices to definitively withdraw the head portion 2 from its enjoinment to the pointed end section 5 of the lancet needle 3.

Furthermore, the vertex or top end of each cam section 7, 9 is axially spaced by a certain limited amount from the associated opposite end face 6 or 8 of the head portion 2 or the base portion 1, respectively. A limiting stop for a lateral displacement of the head portion 2 relative to the base portion 1 or from an axially aligned relationship with the lancet needle 3 is thereby created. Consequently, an intentional or unintentional lateral force exerted on the head portion 2 can only lead to a limited lateral displacement of the head portion 2 from a predeterminded axial alignment. This displacement can be determined by appropriately selecting the spacing between the vertices or top ends of the cam sections 7, 9 and the relevant end face 6, 8 such that damaging effects cannot be induced by such lateral forces on the lancet needle 3, and especially not on the pointed end section 5 thereof embedded in the head portion 2.

The remaining construction of the lancet is known to the skilled person, so that a description of details thereof is not necessary.

The invention has been described hereinabove on the basis of an embodiment wherein the cam sections on the head portion and the base portion are of identical construction. The cam sections of the head portion could however be different from those on the base portion, in that e.g. the cam sections of one of these parts could be formed in the manner of the previously described embodiment whilst the cam sections on the other part could have the configuration of stems or studs protruding axially from the relevant end face and could be provided with rounded top faces. Furthermore, the cam faces of the cam sections need not initiate axial movements by rotation of the head portion in both directions. Rather, separation of the head portion from the base portion could require the application of a rotational force in a specific direction of rotation only. Instead of providing one pair of cam sections on the head portion and another pair of cam sections on the base portion each at a mutual angular spacing of 180°, more than two, e.g. three cam sections could also be provided on each part at an angular spacing of 60°. Finally, the preset breaking zone may be constructed in such a manner that it will be severed when applying a rotational force to the head portion before the cam sections engage with each other such as to initiate an axial movement so that only the axial movement of the head portion relative to the base portion will be controlled by the cam sections. However, the preset breaking point could also be designed such that severing only occurs in the course of the axial movement or is only completed in conjunction therewith.

It will be readily observed from the foregoing detailed description of the present invention that numerous variations and modifications may be made without departing from the true spirit and scope of the novel concepts os principles of the invention.

What is claimed is:

1. A lancet for the extraction of blood, the lancet comprising:
    a base portion of plastics material;
    a lancet needle of a metallic material held in said base portion and having a pointed end section protruding from the base portion;
    a head portion of plastics material integrally connected to the base portion by a preset breaking zone and adapted to be removed from the base portion when said breaking zone is broken for exposing the pointed end section of the lancet needle, the lancet needle being embedded in the head portion prior to the removal thereof; and
    cooperating cam means being provided on said base and head portions, said cam means engaging with each other upon relative rotation between the head and base portions for creating an axial movement of the head portion relative to the base portion thereby exerting an axial force to one of said base and head portions relative to the other for breaking said breaking zone.

2. The lancet according to claim 1, wherein said cam means comprise at least a pair of cam sections on either one of said head and base portions, said pair of cam sections of said head portion being peripherally offset with each other, and said pair of cam sections of said base portion being peripherally offset with each other and relative to the cam sections of said head portion, said cam sections of the head and base portions engaging with each other during rotation of one said head and base portions relative to the other, whereby at least one pair of said pairs of cam sections of the head and base portions having cam guiding faces.

3. The lancet according to claim 2, wherein said cam sections of said head and base portions having top ends spaced from an adjacent one of opposite end faces of said head and base portions for limiting a lateral movement of said head and base portions relative to each other from a coaxial alignment relative to the lancet needle.

4. The lancet according to claim 2, wherein each of said cam sections has a gable-like configuration having a pair of inclined cam faces on opposite sides thereof.

5. The lancet according to claim 1, wherein said cam means are effective for initiating an axial movement upon relative rotation between the head and base portions in at least one direction of rotation.

6. A lancet comprising:

a needle for facilitating extraction of blood;

a base portion for fixedly holding a portion of the needle therein, the base portion having a cam section provided on a surface thereof;

a head portion having a recess formed on a lower surface thereof, the recess being formed such that the recess substantially encases an end of the needle, the head portion having a cam section provided on the lower surface; and a breaking zone for securing the base portion to the head portion, the breaking zone being severed upon a rotational movement of either the base portion or the head portion, wherein the cam section of the base portion and the cam section of the head portion slidably engage each other during the rotational movement of either the base portion or the head portion such that an axial force is generated to thereby displace the head portion away from the base portion to expose the end of the needle, and wherein the axial force is perpendicular to the rotational movement.

7. The lancet according to claim 6, wherein the cam section of the base portion is formed as a projection that extends outwardly from and tapers in a direction away from the surface of the base portion.

8. The lancet according to claim 6, wherein the cam section of the head portion is formed as a projection that extends outwardly from and tapers in a direction away from the lower surface of the head portion.

* * * * *